United States Patent
Grözinger et al.

(10) Patent No.: US 7,812,326 B2
(45) Date of Patent: Oct. 12, 2010

(54) TREATMENT STATION FOR PARTICLE THERAPY

(75) Inventors: Sven Oliver Grözinger, Herzogenaurach (DE); Eike Rietzel, Darmstadt (DE); Tim Use, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 269 days.

(21) Appl. No.: 11/997,989

(22) PCT Filed: Aug. 8, 2006

(86) PCT No.: PCT/EP2006/065128
§ 371 (c)(1), (2), (4) Date: Feb. 5, 2008

(87) PCT Pub. No.: WO2007/020212
PCT Pub. Date: Feb. 22, 2007

(65) Prior Publication Data
US 2008/0191152 A1 Aug. 14, 2008

Related U.S. Application Data

(60) Provisional application No. 60/707,783, filed on Aug. 12, 2005.

(30) Foreign Application Priority Data
Aug. 12, 2005 (EP) .................. 05017626

(51) Int. Cl.
G21K 5/10 (2006.01)
A61N 5/00 (2006.01)
H05H 3/02 (2006.01)

(52) U.S. Cl. .............. 250/492.3; 250/492.22

(58) Field of Classification Search .......... 250/492.3, 250/492.1, 492.22; 376/112; 600/443, 112
See application file for complete search history.

(56) References Cited

U.S. PATENT DOCUMENTS
3,500,043 A 3/1970 Hanssen
(Continued)

FOREIGN PATENT DOCUMENTS
EP 0 986 071 A2 3/2000
(Continued)

OTHER PUBLICATIONS
Written Opinion dated Nov. 2006.
(Continued)

*Primary Examiner*—Nikita Wells
*Assistant Examiner*—Johnnie L Smith
(74) *Attorney, Agent, or Firm*—Brinks, Hofer, Gilson & Lione

(57) ABSTRACT

A treatment station for particle bombardment of a patient is provided. The treatment station includes an apparatus for adaptation of at least one particle beam parameter of a particle beam of a particle therapy installation. The treatment station operates in at least two operating modes, with the treatment station being operable in a first operating mode with a first particle type and in a second operating mode with a second particle type. The apparatus has at least one first beamforming element, which is held by a holding unit. The beamforming element is designed for adaptation of the particle beam parameter. The holding unit positions of the first beamforming element as a function of the operating mode, such that the first beamforming element can be arranged in the particle beam in the first operating mode, and cannot be arranged in the particle beam in the second operating mode.

9 Claims, 3 Drawing Sheets

U.S. PATENT DOCUMENTS

| | | | |
|---|---|---|---|
| 4,112,306 A * | 9/1978 | Nunan | 376/112 |
| 4,528,453 A | 7/1985 | Heller | |
| 5,349,198 A * | 9/1994 | Takanaka | 250/492.3 |
| 5,440,133 A | 8/1995 | Moyers et al. | |
| 6,607,489 B2 * | 8/2003 | Hoctor et al. | 600/443 |
| 2004/0094725 A1 | 5/2004 | Gierak et al. | |
| 2005/0051740 A1 * | 3/2005 | Yanagisawa et al. | 250/492.1 |
| 2005/0127306 A1 * | 6/2005 | Yanagisawa et al. | 250/492.1 |
| 2005/0167616 A1 * | 8/2005 | Yanagisawa et al. | 250/492.22 |
| 2005/0205806 A1 * | 9/2005 | Tadokoro et al. | 250/492.3 |
| 2006/0192146 A1 * | 8/2006 | Yanagisawa et al. | 250/492.1 |

FOREIGN PATENT DOCUMENTS

| | | |
|---|---|---|
| EP | 0986070 | 3/2000 |
| EP | 1 213 744 A2 | 6/2002 |

OTHER PUBLICATIONS

International Search Report dated Nov. 7, 2006.

U. Weber and G. Kraft: "Design and construction of a ripple filter for a smoothed depth dose distribution in conformal particle therapy," Phys. Med. Biol. 44 (1999) 2765-2775.

H. Blattmann in "Beam delivery systems for charged particles," Radiat. Environ. Biophys. (1992) 31:219-231.

Lanza, Gregory M. et al., "Novel Paramagnetic Contrast Agents for Molecular Imaging and Targeted Drug Delivery," Current Pharmaceutical Biotechnology, 2004, vol. 5, No. 6, pp. 495-507.

European Office Written Opinion and Search Report dated Jan. 2006 with English translation.

* cited by examiner

TREATMENT STATION FOR PARTICLE THERAPY

The present patent document is a 35 U.S.C. §371 application of PCT Application Serial Number PCT/EP2006/065128, filed Aug. 8, 2006, designating the United States, which is hereby incorporated by reference. This patent document also claims the benefit of European patent application EP 05017626, filed Aug. 12, 2005, which is hereby incorporated by reference. This patent document also claims the benefit of U.S. patent application 60/707,783, filed Aug. 12, 2005, which is hereby incorporated by reference.

BACKGROUND

The present embodiments relate to a particle therapy installation for acceleration of at least two particle types, in which case a first particle type is accelerated in a first operating mode, and a second particle type is accelerated to in a second operating mode. The present embodiments also relate to a treatment station having an apparatus for adaptation of a particle beam parameter of a particle beam of a particle therapy installation of this type.

EP 0 986 071 A3 discloses an ion beam therapy system, which has two ion sources, an accelerator system with a linear accelerator, and a Synchrotron as well as an ion beam transport system. An ion beam therapy system such as this can be used to accelerate various ion types, and to pass them to treatment stations.

In addition to the provision of two separate ion sources as disclosed by EP 0 986 071 A3, different ions can also be obtained with a configuration in which two ionization apparatuses, such as sources of different ion types, are interchanged and are operated alternately. The expression "particle source" includes either embodiment variants.

During a bombardment session in beam therapy, a patient is positioned at a treatment station, and the patient's positioning is verified with respect to the position on which the therapy plan is based. Bombardment then takes place from one or more incidence directions with particles, for example, protons, pions, helium ions, carbon ions or oxygen ions.

In particle therapy installations, such as those described in EP 0 986 071 A3, passive elements have been placed, generally manually, in a therapy beam path before the start of a bombardment session. For example, ripple filters or range shifters have been placed manually at the beam outlet, depending on the requirements.

A ripple filter is known, for example, from the publication by U. Weber and G. Kraft: "Design and construction of a ripple filter for a smoothed depth dose distribution in conformal particle therapy," Phys. Med. Biol. 44 (1999) 2765-2775.

A scattering system for a charged particle beam is known, for example, from U.S. Pat. No. 5,440,133. The scattering system is designed in such a manner that its thickness can be adjusted uniformly and continuously. For example, two wedges are moved into or out of the beam on opposite sides.

Various bombardment installations and techniques are described by H. Blattmann in "Beam delivery systems for charged particles", Radiat. Environ. Biophys. (1992) 31:219-231. This document describes the use of beamforming elements such as range modulators, collimators and bolus elements. A bolus is used, for example, for range matching of the rear dose distribution to a tumor. Passive elements can also be used for beamforming for particle therapy in conjunction with a raster scanning method.

SUMMARY

The present embodiments may obviate one or more of the drawbacks and limitations inherent in the related art. For example, one embodiment may simplify the procedure for operation of a particle therapy installation, in terms of the use of different particle types.

In another example, one embodiment may simplify particle-specific adaptation of a particle beam parameter of a particle therapy beam.

In one embodiment, the treatment station and the particle therapy installation have an apparatus for adaptation of at least one particle beam parameter of a particle beam of a particle accelerator installation, which can be operated at least in two operating modes. A first particle type is accelerated in a first operating mode, and a second particle type is accelerated in a second operating mode. The apparatus includes a first beamforming element, which is held by a holding unit. The beamforming element is adapted to the particle beam parameter. The holding unit is designed for positioning of the first beamforming element as a function of the operating mode, such that particles pass through the first beamforming element in the first operating mode, and particles do not pass through the first beamforming element in the second operating mode.

The apparatus for adaptation of a particle beam parameter or its use in a particle accelerator installation may eliminate the need for the manual positioning of a beamforming element, which is correspondingly time-consuming, and this can be carried out in an automated form with the aid of the holding unit and an adjusting mechanism. A patient may be bombarded with different particle types without having to manually replace a particle-specific beamforming element. The particle beam may be adapted by a beamforming element, for example, from a therapy control center for the particle therapy installation. This avoids the time-consuming interruption for replacement of beamforming elements.

The apparatus for adaptation of the beam parameter may simplify the bombardment process and reduce the need for monitoring of the bombardment station with an operator being present.

When one embodiment of the apparatus for adaptation of the beam parameter is used in combination with raster scanning methods, this results, for example, in a number of particle-specific beamforming elements which are not patient-specific. The independence of the patient makes it possible to automate the adaptation of the particle therapy installation when changes take place between patients and/or particle types.

In one embodiment, the apparatus has an automatic drive unit for positioning of at least one beamforming element. Position sensors may be provided for monitoring the position of the beamforming element or other elements.

In a one embodiment, the apparatus has a second beamforming element, which is held by the holding unit, influences the same and/or a different beam parameter, is also firmly connected to the first beamforming element or can be moved independently of the first beamforming element and can be positioned in such a manner that particles pass through the second beamforming element in the second operating mode. Particles do not pass through the second beamforming element in the first operating mode. This makes it possible to operate the particle therapy installation automated on a particle-specific basis, since only the beam elements for the respective particle type are moved in an automated manner into the particle beam in the respective operating mode. In this embodiment, when two or more beamforming elements are used, the beam parameters of a plurality of particle types can be modified and adapted on a particle-specific basis. By way of example, possible beamforming elements in this case are ripple filters for widening of the particle energy distribution of the particle beam, a beam collimator for limiting the radial extent of the particle beam, a range shifter for adaptation of the particle energy, a bolus for range matching of the rear dose distribution to a tumor, and a scattering element for beam widening.

BRIEF DESCRIPTION OF THE DRAWINGS

A plurality of exemplary embodiments will be explained in the following text with reference to FIGS. 1 to 6, in which.

DETAILED DESCRIPTION

Figure 1:
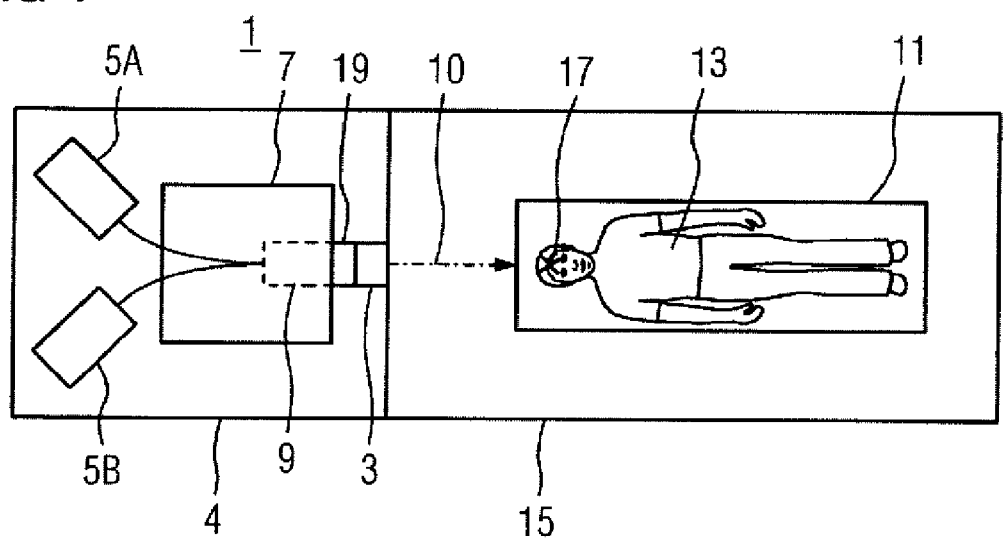
FIG. 1 shows a schematically illustrated particle therapy installation.

FIG. 1 shows a particle therapy installation 1 (treatment station). An apparatus 3 is used in this installation for adaptation of a beam parameter (e.g., forming a particle beam).

The particle therapy installation 1 has two particle sources 5A and 5B and a vacuum beam-guidance and acceleration system 7 on the accelerator side 4. The particle therapy installation 1 also has, by way of example, a raster scanning apparatus 9. A configuration such as this is designed to accelerate different particle types from the particle sources 5A and 5B to energy levels of several hundred MeV, and to supply them to at least one beam therapy station 15.

During the bombardment process, a particle beam 10 is aimed at a patient 13 who is positioned on a couch (support) 11. The beam therapy station 15 has a patient positioning apparatus (not shown) which allows the patient 13 to be positioned with the tissue to be bombarded at an isocenter 17 of the beam therapy station 15. The particle beam 10 may pass through the isocenter 17 with the raster scanning apparatus 9 at a null position.

For beam monitoring purposes, the particle therapy installation 1 also has a beam monitoring system 19 which, for example, monitors the beam position and the beam intensity. The beam monitoring system 19 is arranged between the patient 13 and the beam outlet of the vacuum beam-guidance and acceleration system 7. The apparatus 3 for adaptation of at least one particle beam parameter may be arranged downstream from the beam monitoring system 19 in the beam direction. This allows a particle beam parameter to be matched to the respectively currently used particle type, that is to say it provides beamforming elements for different particle types.

The apparatus 3 may have a compact design in order to occupy as little space as possible and to be easily accessible from the outside, for example, for maintenance purposes.

The apparatus 3 allows beamforming elements to be positioned on a particle-specific basis as a function of the operating mode such that, for example, particles pass through a first beamforming element in the first operating mode and particles do not pass through the first beamforming element in the second operating mode, and such that particles do not pass through a second beamforming element in the first operating mode, and particles do pass through the second beamforming element in the second operating mode. The beamforming elements are positioned as required in the particle beam, for example, in the scanning area in the path of the particle beam.

Figure 2:
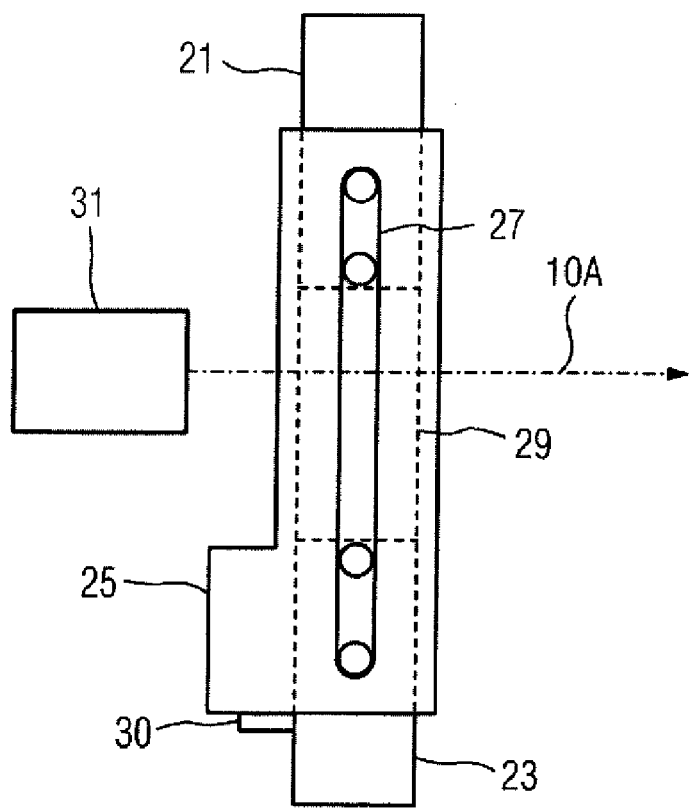
FIGS. 2 and 3 shows one embodiment of an apparatus for adaptation of a particle beam parameter.

FIG. 2 shows an apparatus 3 in which two beamforming elements 21, 23 can be moved on a plane independently of one another. The beamforming elements 21, 23 are held by a holding unit 25 which, for example, has a guidance system 27. The beamforming elements 21 and 23 are moved individually between a parked position and a beam position 29, with the aid of a drive apparatus 28 (see FIG. 3). The beamforming elements 21 and 23 are located in their parked positions in FIG. 2. The positions assumed are detected by sensors, for example, by a sensor 30.

FIG. 2 shows a beam outlet 31 from the vacuum beam-guidance and acceleration unit, and a particle beam 10A. The actual position of the beamforming element or elements 21, 23 may be monitored continuously (for example, by an encoder) or discretely (for example, by a limit switch, in this case the sensor 30), by at least one independent sensor.

Figure 3:
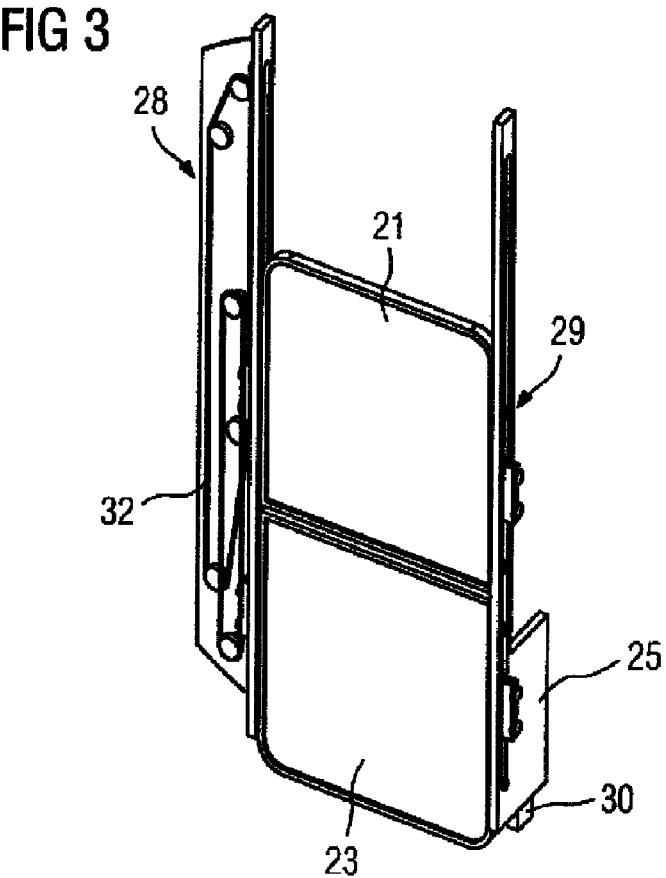

FIG. 3 shows a three-dimensional illustration of the apparatus 3 from FIG. 2 in an operating mode in which particles pass through one of the beamforming elements. By way of example, the beamforming element 21 has been moved to the beam position 29 by the drive apparatus 28. The drive apparatus 28 has, for example, a belt system 32 which is driven by an electric motor.

Figure 4:
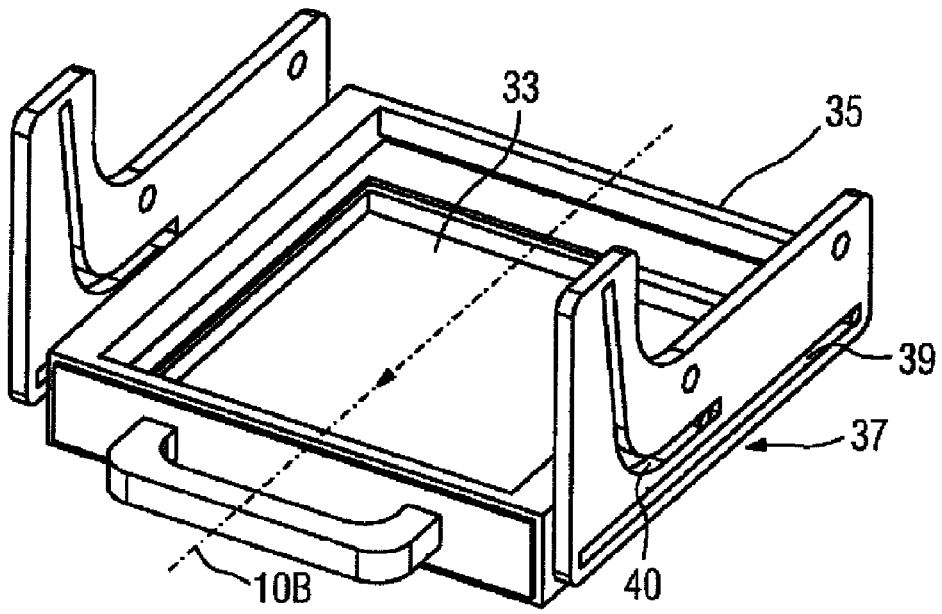
FIGS. 4 and 5 shows one embodiment of an apparatus.
Figure 5:
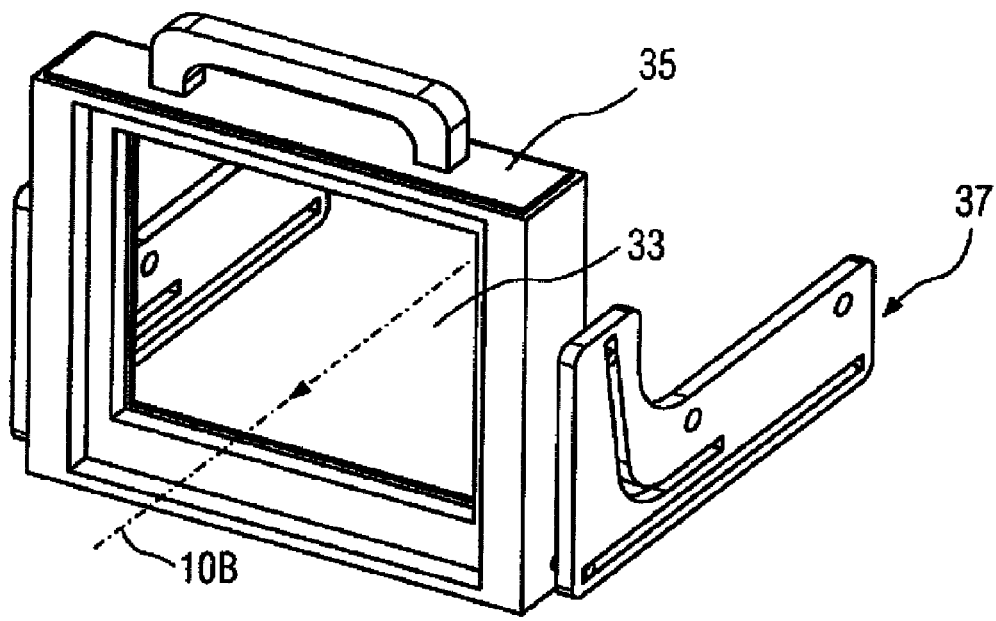

In one embodiment, as shown in FIGS. 4 and 5, a beamforming element 33, for example, a ripple filter, can be folded into and out of a horizontally running particle beam 10B (to be more precise into one possible beam path). The beamforming element 33 is mounted in a frame 35 for this purpose. In FIG. 3, the beamforming element 33 is located in a horizontal parked position, from which it can be moved to a vertical beam position by a cam drive 37. The drive is provided, for example, via an electric motor (which is not shown) by translation of the frame 35 in a lower guide rail 39. The shape of an upper guide rail 40 results in the frame 35 being folded from the lower horizontal parked position to the vertical beam position shown in FIG. 5. The position change is reversible. The position change may be carried out quickly because of the short movement distance. This embodiment requires space essentially only in the beam direction. Position monitoring is carried out, for example, once again by limit switches, which indicate the parked position and the beam position. An encoder can optionally be used to determine the position continuously.

Figure 6:
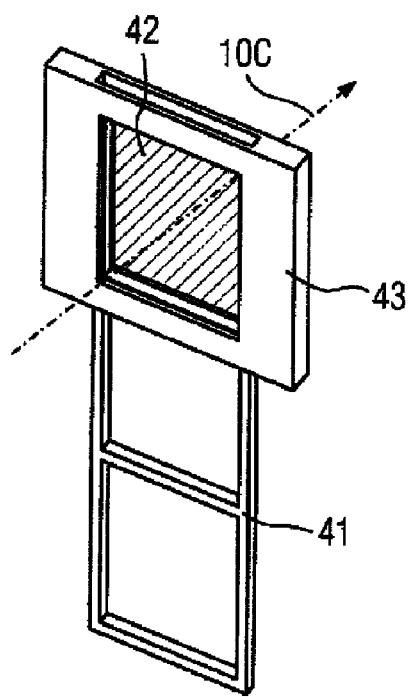
FIGS. 6 and 7 shows one embodiment of an apparatus.
Figure 7:
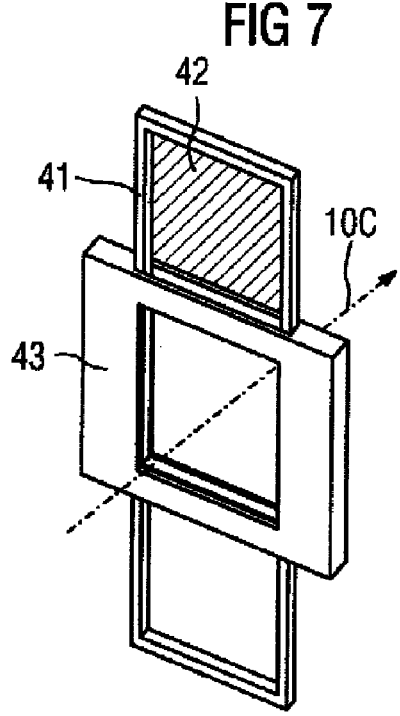

In one embodiment, as shown in FIGS. 6 and 7, a frame structure 41 is used, which has space for at least one passive beamforming element 42. The frame structure 41 may also include an empty position (i.e., without a beamforming element). One beamforming element may be provided for each particle type, and the beamforming elements are separated from one another by a fixed distance in the frame 41. Beamforming elements (or else no beamforming element) are positioned on a particle-specific basis in the particle beam by movement of the frame structure 41 along a guide 43. In one embodiment, frame areas which are located outside the guide 43 can be folded away at the side. In this case, the frame structure can be driven, for example, by an electric motor. The position change of the beamforming elements is reversible, automated and can be carried out quickly. The position of the frame structure 41 may be determined continuously or discretely.

The automation of the position changing and replacement process and the use of beamforming elements which are designed for different particle types may make it possible to adjust a particle therapy installation for different bombardment modes with different particle types in a short time. This avoids the time-consuming manual intervention of an operator, reduces the time for which a patient has to stay in the beam therapy station, and increases the patient throughput. The particle bombardment of a patient may be optimized on a particle-specific basis with respect to the procedure, and incorrect beamforming element fits can be avoided by the automatic driving and monitoring of the apparatus.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A treatment station for particle therapy of a patient comprising:
    an apparatus for adjusting a particle beam parameter of a particle beam of a particle therapy installation, the apparatus comprising:
        a first beamforming element configured to adjust the particle beam parameter;
        a holding unit that holds the first beamforming element and positions the first beamforming element as a function of an operating mode of the treatment station,
    wherein the treatment station has a first operating mode with a first particle type and a second operating mode with a second particle type, and
    wherein the holding unit positions the first beamforming element as a function of the operating mode of the treatment station, such that the first beamforming element is arranged in the particle beam in the first operating mode, and is not arranged in the particle beam in the second operating mode.

2. The treatment station as claimed in claim 1, wherein the apparatus for adjusting the particle beam parameter comprises an automatic drive unit configured to position the first beamforming element, the automatic drive unit communicating with position sensors for monitoring the position of the beamforming element.

3. The treatment station as claimed in claim 1, wherein the apparatus for adjusting the particle beam parameter comprises a second beamforming element, which is held by the holding unit and adjusts the particle beam parameter, another particle beam parameter, or the particle beam parameter and the another particle beam parameter,
    wherein the second beamforming element is firmly connected to the first beamforming element and is configured to move independently of the first beamforming element, and
    wherein the holding unit positions the second beamforming element as a function of the operating mode of the treatment station, such that the second beamforming element is arranged in the particle beam in the second operating mode, and is not arranged in the particle beam in the first operating mode.

4. The treatment station as claimed in claim 3, wherein at least one of the first beamforming element and the second beamforming element is a ripple filter for widening of the particle energy distribution of the particle beam, a beam collimator, a range shifter, a bolus or a scattering element.

5. A particle therapy installation for acceleration of at least two particle types, comprising:
    a treatment station for bombardment of a patient with particles, the treatment station including an apparatus for adjusting a beam parameter of a particle beam of the particle therapy installation,
    wherein the apparatus for adjusting the beam parameter is configured to allow a first particle type for particle therapy to be supplied to the treatment station in a first operating mode and allow a second particle type for particle therapy to be supplied to the treatment station in a second operating mode.

6. The particle therapy installation as claimed in claim 5, wherein the apparatus for adjusting the beam parameter comprises:
    a beamforming element held by a holding unit;
    an automatic drive unit that positions the beamforming element, and
    a position sensor communicating with the automatic drive unit for monitoring the position of the beamforming element.

7. The particle therapy installation as claimed in claim 6, comprising a first particle source and a second particle source for production of the at least two particle types, and a vacuum beam-guidance and acceleration system for particle acceleration,
    wherein the apparatus for adjusting the beam parameter is arranged in a particle beam profile close to a patient after the emergence of the particle beam from the vacuum beam-guidance and acceleration system.

8. The particle therapy installation as claimed in claim 6, comprising a second beamforming element, which is held by the holding unit and adjusts the beam parameter, the another beam parameter, or the beam parameter and the another beam parameter,
    wherein the second beamforming element is firmly connected to the first beamforming element or is moved independently of the first beamforming element, and
    wherein the second beamforming element is positioned, such that particles pass through the second beamforming element in the second operating mode, but particles do not pass through the second beamforming element in the first operating mode.

9. The particle therapy installation as claimed in claim 6, wherein the beamforming element is a ripple filter for widening of the particle energy distribution of the particle beam, a beam collimator, a range shifter, a bolus or a scattering element.

* * * * *